(12) United States Patent
Tatsuka et al.

(10) Patent No.: US 6,759,212 B1
(45) Date of Patent: Jul. 6, 2004

(54) CELL CYCLE-REGULATING PROTEINS

(75) Inventors: Masaaki Tatsuka, Hiroshima-ken (JP); Yasuhiko Terada, Osaka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/485,534

(22) PCT Filed: Aug. 17, 1998

(86) PCT No.: PCT/JP98/03641

§ 371 (c)(1), (2), (4) Date: Feb. 14, 2000

(87) PCT Pub. No.: WO99/09160

PCT Pub. Date: Feb. 25, 1999

(30) Foreign Application Priority Data

Aug. 15, 1997 (JP) ............................................. 9-235371

(51) Int. Cl.$^7$ ........................... C12N 5/10; C12N 15/00; C12N 15/63; C07H 21/04
(52) U.S. Cl. ................. 435/69.1; 435/252.3; 435/320.1; 435/325; 536/23.1; 536/23.5; 536/24.5
(58) Field of Search ............................... 536/23.1, 23.5, 536/24.5, 325; 435/69.1, 320.1, 252.3

(56) References Cited

U.S. PATENT DOCUMENTS 5,962,312 A * 10/1999 Plowman et al.

FOREIGN PATENT DOCUMENTS

WO          97/22702        6/1997

OTHER PUBLICATIONS

Varmus, H., "Historical Review of Oncogenesis" in Oncogenes and the Molecular Origins of Cancer, 1989, p. 36.*
Hagemeijer, A, "Cytogenetics and Oncogenes", Leukemia, 1992, vol. 6, Suppl. 4, pp. 16–18.*
Alberts et al, The Molecular Biology of the Cell (textbook), 2nd ed., 1989, p. 1203.*
Sheeny et al, Cancer Research, 1974, vol. 34, pp. 991–996.*
Demidova et al, "A comparative study of primary human cell cultures of diffuse goiter and cancer or the thyroid gland", Voprosy Onkologii, 1975, vol. 21, pp. 833–88, (Abstract only).*
Takeichi et al, "Studies on tumors produced by cells transformed with herpes simplex virus type–2", Gann, 1977, vol. 68, pp. 653–661, (abstract only).*
Burgess et al, "Possible Dissociation of the Heparin–binding and Mitogenic Activities of Heparin–binding Growth Factor–1", Journal of Cell biology, 1990, vol. 111, pp. 2129–2138.*
Lazar et al, "Transforming growth factor–alpha: mutation of aspartic acid 47 and leucine 48 results in different biological activities", Molecular and Cellular biology, 1988, vol. 8, pp. 1247–1252.*

Branch, A., "A hitchhiker's guide to antisense and nonantisense biochemical pathways", Hepatology, 1996, vol. 24, pp. 1517–1529.*
Broaddus et al, "Strategies for the design and delivery of antisense oligonucleotides in central nervous system", Methods in Enzymology, vol. 314, pp. 121–135.*
M. Shindo et al., "cDNA Cloning, Expression, Subcellular Localization, and Chromosomal Assignment of Mammalian Aurora Homologues, Aurora–Related Kinase (ARK) 1 and 2", Biochemical and Biophysical Research Communications, 1998 by Academic Press, vol. 244, (285–292).
Y. Terada et al., "AIM–1: A mammalian midbody–associated protein required for cytokinesis" EMBO Journal, Oxford University Press, 1998 vol. 17, (667–676).
Kuniya Abe, "Rapid isolatio of desired sequences from lone linker PCR amplified cDNA mixtures: Application to identification and recovery of expressed sequences in cloned genomic DNA.", Mammalian Genome vol. 2, pp. 252–259, 1992.
Fioina J. Clay et al., "Identification and cloning of a protein kinase–encoding mouse gene, Plk, related to the polo gene of Drosophila.", Proceedings of the National Academy of Science, vol. 90, pp. 4882–4886, 1993.
Brian Fenton et al., "A conserved mitotic kinase active at late anaphase–telophase in syncytial Drosophila embryos.", Nature, vol. 363, pp. 637–640, 1993.
Leigh Francisco et al., "Type 1 Protein Phosphatase Acts in Opposition to IpI1 Protein Kinase in Regulating Yeast Chromosome Segregation.", Molecular and Cellular Biology, pp. 4731–4740, 1994.
Hironori Funabiki et al., "Cut2 proteolysis required for sister–chromatid separation in fission yeast.", Nature, vol. 381, pp. 438–441, 1996.
Michael Glotzer et al., "Cyclin is degraded by the ubiquitin pathway.", Nature, vol. 349, pp. 132–138, 1991.

(List continued on next page.)

*Primary Examiner*—Karen A. Canella
(74) *Attorney, Agent, or Firm*—Foley & Lardner

(57) ABSTRACT

A DNA containing a nucleotide sequence encoding the amino acid sequence shown as SEQ ID NO: 2 in Sequence Listing, or a nucleotide sequence encoding a protein having the amino acid sequence shown as SEQ ID NO: 2 in Sequence Listing with partial substitution, deletion or addition and having cell cycle control activity, or a nucleotide sequence hybridizing to them; a recombinant vector containing said DNA; a cell transformed with said vector; a process for producing AIM-1 using said DNA; a recombinant AIM-1 protein obtained by said process; an oligonucleotide or peptide nucleic acid capable of specifically hybridizing to a nucleotide sequence encoding AIM-1 protein; an antibody recognizing AIM-1; a therapeutic agent for diseases associated with abnormal cell growth containing an inhibitor against AIM-1 protein; and a screening method for materials having serine-threonine inhibitory activity using AIM-1 gene or AIM-1 protein.

6 Claims, 5 Drawing Sheets

OTHER PUBLICATIONS

David M. Glover et al., "Mutations in aurora Prevent Centrosome Separation Leading to the Formation of Monopolar Spindles.", Cell, vol. 81, pp. 95–105, 1995.

Lawrence S. B. Goldstein, "The kinesin superfamily: tails of functional redundancy.", Trends in Cell biology, vol. 1, pp. 93–99, 1991.

Roy M. Golsteyn et al., "Cell Cycle Regulation of the Activity and Subcellular Localization of PLK1, a Human Protein Kinase Implicated in Mitotic Spindle Function.", The Journal of Cell Biology, vol. 129, No. 6, pp. 1617–1628, 1995.

Manfred Gossen et al., "Tight control of gene expression in mammalian cells by tetracycline responsive promoters.", Proceedings of the National Academy of Science, vo. 89, pp. 5547–5551, 1992.

Steven K. Hanks et al., "The Protein Kinase Family: Conserved Features and Deduced Phylogeny of the Catalytic Domains.", Science, vol. 241, pp. 42–52, 1988.

Margaret M. S. Heck et al., "The Kinesin–like Protein KLP61F Is Essential for Mitosis in Drosophila.", The Journal of Cell Biology, vol. 123, No. 3, pp. 665–679, 1993.

Kyung S. Lee et al., "Plk Is an M–Phase–Specific Protein Kinase and Interacts with a Kinesin–Like Protein, CHO1/MKLP–1.", Molecular and Cellular Biology, pp. 7143–7151, 1995.

Hirohisa Masuda et al., "Role of γ–tubulin in mitosis specific microtubule nucleation from the Schizosaccharomyces pombe spindle pole body.", Journal of Cell Science, vol. 109, pp. 165–177, 1996.

Seiichi Mizushima et al., "pEF–BOS, a powerful mammalian expression vector.", Nucleic Acids Research, vol. 18, No. 17, pg. 5322, 1990.

Jonathan D. Moore et al., "Kinesin proteins: a phylum of motors for microtubule–based motility.", BioEssays, vol. 18, No. 3, pp. 207–219,, 1995.

Masayuki Otsu et al., "Isolation of two members of the rat MAP kinase kinase gene family.", FEBS letters, vol. 320, No. 3, pp. 246–250, 1993.

Hong–Bing Shu et al., "A transient association of γ–tubulin at the midbody is required for the completion of cytokinesis during the mammalian cell division.", Journal of Cell Science, vol. 108, pp. 2955–2962, 1995.

Alice Wang et al., "Site–Specific Mutagenesis of the Human Interleukin–2 Gene: Structure–Function Analysis of the Cysteine Residues.", Science, vol. 224, pp. 1431–1433, 1984.

Byron C. Williams et al., "Th Drosophila Kinesin–like Protein KLP3A Is a Midbody component Required for Central Spindle Assembly and Initiation of Cytokinesis.", The Journal of Cell Biology, vol. 129, No. 3, pp. 709–723, 1995.

Niwa, et al. "Cell–cycle–dependent expression of the STK–1 gene encoding a novel murine putative protein Kinase", Gene (1996) vol. 169 P 197–201.

Kimura, et al. "Isolation and characterization of a cDNA encoding a human novel serine/threonine kinase, aik", Molecular Biology of the Cell (1996) vol. 7 p. 562A.

Sen, et al. "A putative serine/threonine kinase encoding gene BTAK on chromosome 20q13 is amplified and overexpressed in human breast cancer cell lines", Oncogene (Mar., 1997) vol. 14, No. 18 pp. 2195–2220.

Francisco, et al. "Type 1 protein phosphatase acts in opposition to Ip11 protein kinase in regulating yeast chromosome segregation," olecular and Cellular Biology (1994) vol. 14, No. 7 pp. 4731–4740.

Kimura, et al. Cell cycle–dependent expression and spindle pole localization of a novel human protein kinase, Aik, related to aurora of drosophila and yeast Ip11, The J. of Biological chemistry (1997) vol. 272,(21) 13766–13771.

Qiam, et al. "The IPL gene on chromosome 11p15.5 is imprinted in humans and mice and is similar to 29 TDAG51, implicated in Fas expression and apoptosis", Human Molecular Genetics (1997) vol. 6, (12) p. 2021–2029.

* cited by examiner

FIG. 1

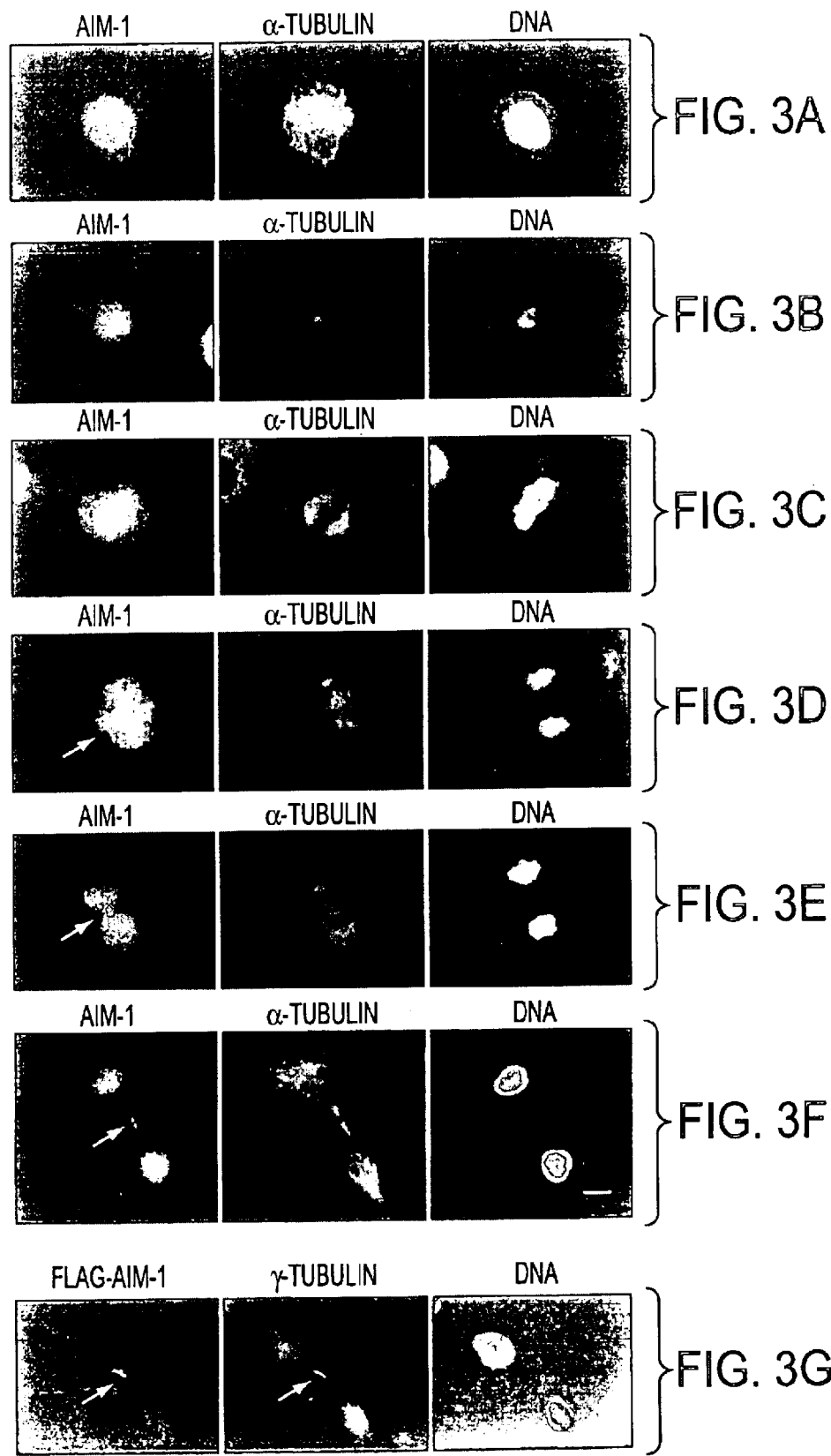

SEQUENCE LISTING

<160> NUMBER OF SEQ ID NOS: 19

<210> SEQ ID NO 1
<211> LENGTH: 84
<212> TYPE: DNA
<213> ORGANISM: Rattus sp.
<220> FEATURE:
<221> NAME/KEY: CDS
<222> LOCATION: (1)..(84)

<400> SEQUENCE: 1

```
att cac aga gac ata aag ccc gag aac ctg ctg tta ggt cta cag gga     48
Ile His Arg Asp Ile Lys Pro Glu Asn Leu Leu Leu Gly Leu Gln Gly
  1               5                  10                  15 gag ctg aag att gcg gac ttt ggc tgg tct gtg cat                     84
Glu Leu Lys Ile Ala Asp Phe Gly Trp Ser Val His
             20                  25
```

<210> SEQ ID NO 2
<211> LENGTH: 28
<212> TYPE: PRT
<213> ORGANISM: Rattus sp.

<400> SEQUENCE: 2

```
Ile His Arg Asp Ile Lys Pro Glu Asn Leu Leu Leu Gly Leu Gln Gly
  1               5                  10                  15

Glu Leu Lys Ile Ala Asp Phe Gly Trp Ser Val His
             20                  25
```

<210> SEQ ID NO 3
<211> LENGTH: 1815
<212> TYPE: DNA
<213> ORGANISM: Rattus sp.
<220> FEATURE:
<221> NAME/KEY: CDS
<222> LOCATION: (185)..(1213)

<400> SEQUENCE: 3

```
attcgaaagt gttcgggtcg cggggtaggt tctccggtgt acgagcgccc atcggactag     60
gtttcggctt ttccggggac tccggaggcc gcagtgatcc tcggggtcgg gttccgttgg    120
gcgggtccac gtgcccgccg atccgcctag aaggagagct cccctcccgc ttttgccctg    180 gaga atg gct cag aaa gag aac gtc tac ccg tgg ccc tac ggc tca aag    229
     Met Ala Gln Lys Glu Asn Val Tyr Pro Trp Pro Tyr Gly Ser Lys
       1               5                  10                  15 acg tct caa tct ggc ctg aac acc ttg ccc cag aga gtc cta cgg aag    277
Thr Ser Gln Ser Gly Leu Asn Thr Leu Pro Gln Arg Val Leu Arg Lys
             20                  25                  30 gag cct gcc gtg aca cct gca cag gcc ctc atg aac cgg tcc aac agc    325
Glu Pro Ala Val Thr Pro Ala Gln Ala Leu Met Asn Arg Ser Asn Ser
         35                  40                  45 cag tcc aca gct gtc cct ggt cag aag ttg act gag aac aag ggt gcc    373
Gln Ser Thr Ala Val Pro Gly Gln Lys Leu Thr Glu Asn Lys Gly Ala
     50                  55                  60 act gcc ttg caa gga tcc cag agc agg cag cct ttc acc att gac aac    421
Thr Ala Leu Gln Gly Ser Gln Ser Arg Gln Pro Phe Thr Ile Asp Asn
 65                  70                  75 ttt gag att ggg cgt cct ctg ggc aaa ggc aaa ttt gga aat gtg tac    469
Phe Glu Ile Gly Arg Pro Leu Gly Lys Gly Lys Phe Gly Asn Val Tyr
 80                  85                  90                  95 ttg gct cgg gag aag aaa agc cgt ttc atc gtg gcg cta aag atc ctc    517
```

-continued

| | |
|---|---|
| Leu Ala Arg Glu Lys Lys Ser Arg Phe Ile Val Ala Leu Lys Ile Leu<br>100                    105                110 | |
| ttc aag tct cag att gaa aag gag ggg gtg gag cac cag ctc cgc cga<br>Phe Lys Ser Gln Ile Glu Lys Glu Gly Val Glu His Gln Leu Arg Arg<br>              115                120                125 | 565 |
| gag atc gaa atc cag gcg cac ctg aaa cat ccc aat att ctt cag ctg<br>Glu Ile Glu Ile Gln Ala His Leu Lys His Pro Asn Ile Leu Gln Leu<br>     130                135                140 | 613 |
| tac aac tac ttc tat gac cag cag agg atc tac ttg ata ctc gaa tac<br>Tyr Asn Tyr Phe Tyr Asp Gln Gln Arg Ile Tyr Leu Ile Leu Glu Tyr<br>145                    150                155 | 661 |
| gcc ccc cgc gga gag ctc tac aag gaa cta cag aag agc gga acc ttc<br>Ala Pro Arg Gly Glu Leu Tyr Lys Glu Leu Gln Lys Ser Gly Thr Phe<br>160                    165                170                175 | 709 |
| gat gag cag cgg act gcc acg atc atg gag gaa ctg tca gac gcg ctg<br>Asp Glu Gln Arg Thr Ala Thr Ile Met Glu Glu Leu Ser Asp Ala Leu<br>              180                185                190 | 757 |
| atg tac tgc cac aag aag aag gtg att cac aga gac ata aag ccc gag<br>Met Tyr Cys His Lys Lys Lys Val Ile His Arg Asp Ile Lys Pro Glu<br>                  195                200                205 | 805 |
| aac ctg ctg tta ggt cta cag gga gag ctg aag att gcg gac ttt ggc<br>Asn Leu Leu Leu Gly Leu Gln Gly Glu Leu Lys Ile Ala Asp Phe Gly<br>            210                215                220 | 853 |
| tgg tct gtg cat gcc cca tcc ctg agg agg aag acc atg tgc ggc acc<br>Trp Ser Val His Ala Pro Ser Leu Arg Arg Lys Thr Met Cys Gly Thr<br>225                    230                235 | 901 |
| ctg gac tat ctg ccc cca gag atg att gaa ggg cgg atg cat aat gag<br>Leu Asp Tyr Leu Pro Pro Glu Met Ile Glu Gly Arg Met His Asn Glu<br>240                    245                250                255 | 949 |
| atg gta gat ctg tgg tgc att gga gtg ctc tgc tat gaa ctg atg gtg<br>Met Val Asp Leu Trp Cys Ile Gly Val Leu Cys Tyr Glu Leu Met Val<br>                      260                265                270 | 997 |
| ggg aac cca ccc ttt gag agc cct agc cac agt gag aca tat cgt cgg<br>Gly Asn Pro Pro Phe Glu Ser Pro Ser His Ser Glu Thr Tyr Arg Arg<br>           275                280                285 | 1045 |
| att gtc aag gta gac ctg aag ttt ccc tct tct atg cct ttg ggg gcc<br>Ile Val Lys Val Asp Leu Lys Phe Pro Ser Ser Met Pro Leu Gly Ala<br>                  290                295                300 | 1093 |
| aag gac ctc atc tcc aag ctg ctc aaa cat aac ccc tca caa cga ctg<br>Lys Asp Leu Ile Ser Lys Leu Leu Lys His Asn Pro Ser Gln Arg Leu<br>305                    310                315 | 1141 |
| cct ctg gag cag gtc tcg gct cac cct tgg gtc cgg gcc aac tca cgg<br>Pro Leu Glu Gln Val Ser Ala His Pro Trp Val Arg Ala Asn Ser Arg<br>320                    325                330                335 | 1189 |
| agg gtt ctg cct ccc tct gcc ctt tagcctgctt cttgattttt gttcctgtca<br>Arg Val Leu Pro Pro Ser Ala Leu<br>                     340 | 1243 |
| tttctcagtt ttctttgtat gtctgtgtat gtgtcgtgag aagggggatta gtgattggaa | 1303 |
| actatcccta accccagttc tagggaatct tattccttgg ggatcttatt cctcttctga | 1363 |
| cctctacagg caaaatttggg catacatgtc gtacacatat atgcaagcca aacatataaa | 1423 |
| gttaaaaaac aaacagtgct agagagatgg cttggcagtt aaaagcactg gctactcttc | 1483 |
| ccaagaacca ggagttcaat ttgagcacta caatggtgct cacaaccact gtctgtaaca | 1543 |
| cctaattctg gggtatcgag gccttcaagc ctctgcaggc tagaggctag gatgtggtat | 1603 |
| catcctatgc agggcaagac acccatgcac agaatttttaa atcctctaaa tgaaagaatt | 1663 |
| tgtcaaatgt tgaacgtcat tttaaaaata ctataagcca aaaatgcatt taatacaatt | 1723 |

```
tttctctgaa acatggttta gcctactctg tttaaattc aggaaaatta tgaagaataa    1783
agcatatttt ataataaact cttaaatatt tc                                 1815
```

<210> SEQ ID NO 4
<211> LENGTH: 343
<212> TYPE: PRT
<213> ORGANISM: Rattus sp.

<400> SEQUENCE: 4

```
Met Ala Gln Lys Glu Asn Val Tyr Pro Trp Pro Tyr Gly Ser Lys Thr
 1               5                  10                  15

Ser Gln Ser Gly Leu Asn Thr Leu Pro Gln Arg Val Leu Arg Lys Glu
             20                  25                  30

Pro Ala Val Thr Pro Ala Gln Ala Leu Met Asn Arg Ser Asn Ser Gln
         35                  40                  45

Ser Thr Ala Val Pro Gly Gln Lys Leu Thr Glu Asn Lys Gly Ala Thr
     50                  55                  60

Ala Leu Gln Gly Ser Gln Ser Arg Gln Pro Phe Thr Ile Asp Asn Phe
 65                  70                  75                  80

Glu Ile Gly Arg Pro Leu Gly Lys Gly Lys Phe Gly Asn Val Tyr Leu
                 85                  90                  95

Ala Arg Glu Lys Lys Ser Arg Phe Ile Val Ala Leu Lys Ile Leu Phe
            100                 105                 110

Lys Ser Gln Ile Glu Lys Glu Gly Val Glu His Gln Leu Arg Arg Glu
        115                 120                 125

Ile Glu Ile Gln Ala His Leu Lys His Pro Asn Ile Leu Gln Leu Tyr
    130                 135                 140

Asn Tyr Phe Tyr Asp Gln Gln Arg Ile Tyr Leu Ile Leu Glu Tyr Ala
145                 150                 155                 160

Pro Arg Gly Glu Leu Tyr Lys Glu Leu Gln Lys Ser Gly Thr Phe Asp
                165                 170                 175

Glu Gln Arg Thr Ala Thr Ile Met Glu Glu Leu Ser Asp Ala Leu Met
            180                 185                 190

Tyr Cys His Lys Lys Val Ile His Arg Asp Ile Lys Pro Glu Asn
        195                 200                 205

Leu Leu Leu Gly Leu Gln Gly Glu Leu Lys Ile Ala Asp Phe Gly Trp
    210                 215                 220

Ser Val His Ala Pro Ser Leu Arg Arg Lys Thr Met Cys Gly Thr Leu
225                 230                 235                 240

Asp Tyr Leu Pro Pro Glu Met Ile Glu Gly Arg Met His Asn Glu Met
                245                 250                 255

Val Asp Leu Trp Cys Ile Gly Val Leu Cys Tyr Glu Leu Met Val Gly
            260                 265                 270

Asn Pro Pro Phe Glu Ser Pro Ser His Ser Glu Thr Tyr Arg Arg Ile
        275                 280                 285

Val Lys Val Asp Leu Lys Phe Pro Ser Ser Met Pro Leu Gly Ala Lys
    290                 295                 300

Asp Leu Ile Ser Lys Leu Leu Lys His Asn Pro Ser Gln Arg Leu Pro
305                 310                 315                 320

Leu Glu Gln Val Ser Ala His Pro Trp Val Arg Ala Asn Ser Arg Arg
                325                 330                 335

Val Leu Pro Pro Ser Ala Leu
            340
```

```
<210> SEQ ID NO 5
<211> LENGTH: 7
<212> TYPE: PRT
<213> ORGANISM: Unknown Organism
<220> FEATURE:
<223> OTHER INFORMATION: Description of Unknown Organism: Amino acid
      motif

<400> SEQUENCE: 5

Met His Arg Asp Val Lys Pro
 1               5

<210> SEQ ID NO 6
<211> LENGTH: 7
<212> TYPE: PRT
<213> ORGANISM: Unknown Organism
<220> FEATURE:
<223> OTHER INFORMATION: Description of Unknown Organism: Amino acid
      motif

<400> SEQUENCE: 6

Asp Phe Gly Val Ser Gly Gln
 1               5

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Primer
<223> OTHER INFORMATION: "n" bases at various positions may be t, c,
      a or g

<400> SEQUENCE: 7
atgcaymgng aygtnaarcc                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Primer
<223> OTHER INFORMATION: "n" bases at various positions may be t, c,
      a or g

<400> SEQUENCE: 8
tgnccngana cnccraartc                                              20

<210> SEQ ID NO 9
<211> LENGTH: 54
<212> TYPE: DNA
<213> ORGANISM: Artificial Sequence
<220> FEATURE:
<223> OTHER INFORMATION: Description of Artificial Sequence: Primer

<400> SEQUENCE: 9
agagaattca tggactacaa ggacgatgac gacaagatgg ctcagaaaga gaac         54

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 10
cttgaagagg atccttagcg ccacgat                                      27
```

```
<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 11
atcgtggcgc taaggatcct cttcaag                                          27

<210> SEQ ID NO 12
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 12
gactcagact aaagggcaga gggaggcaga cggcgcgc                              38

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Primer
<223> OTHER INFORMATION: "n" bases at various positions may be t, c,
      a or g

<400> SEQUENCE: 13
athcaymgng ayathaarcc n                                                21

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Primer
<223> OTHER INFORMATION: "n" bases at various positions may be t, c,
      a or g

<400> SEQUENCE: 14
rtgnacngac canccraart                                                  20

<210> SEQ ID NO 15
<211> LENGTH: 12
<212> TYPE: PRT
<213> ORGANISM: Unknown Organism
<220> FEATURE:
<223> OTHER INFORMATION: Description of Unknown Organism: Amino acid
      motif

<400> SEQUENCE: 15

Asn Leu Leu Leu Gly Leu Lys Gly Glu Leu Lys Ile
  1               5                  10

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 16
aatctgctct tagggctcaa gggagagctg aagatt                                36
```

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 17
tccactaata tcggccacgc gtcgactagt ac                                      32

<210> SEQ ID NO 18
<211> LENGTH: 436
<212> TYPE: PRT
<213> ORGANISM: Drosophia sp.

<400> SEQUENCE: 18

Met Ser His Pro Ser Asp His Val Leu Arg Pro Lys Glu Asn Ala Pro
 1               5                  10                  15

His Arg Met Pro Glu Lys Ser Ala Ala Val Leu Asn Met Gln Lys Asn
            20                  25                  30

Leu Leu Leu Gly Lys Lys Pro Asn Ser Glu Asn Met Ala Pro Asp Ser
        35                  40                  45

Lys Pro Leu Pro Gly Ser Ser Gly Ala Leu Ile Arg Ser Ala Ala Thr
    50                  55                  60

Thr Val Arg Pro Ala Thr Lys Pro Gly Leu Gly Ser Ala Ala Thr Thr
65                  70                  75                  80

Val Arg Pro Ala Thr Lys Pro Gly Leu Gly Gly Ser Asn Ser Ile Ala
                85                  90                  95

Ser Ser Glu Gly Asn Asn Phe Gln Lys Pro Met Val Pro Ser Val Lys
            100                 105                 110

Lys Thr Thr Ser Glu Phe Ala Ala Pro Ala Val Ala Pro Ile Lys
        115                 120                 125

Lys Pro Glu Ser Leu Ser Lys Gln Lys Pro Thr Ala Ala Ser Ser Glu
    130                 135                 140

Ser Ser Lys Glu Leu Gly Ala Ala Ser Ser Ala Glu Lys Glu Lys
145                 150                 155                 160

Thr Lys Thr Glu Thr Gln Pro Gln Lys Pro Lys Lys Thr Trp Glu Leu
                165                 170                 175

Asn Asn Phe Asp Ile Gly Arg Leu Leu Gly Arg Gly Lys Phe Gly Asn
            180                 185                 190

Val Tyr Leu Ala Arg Glu Lys Glu Ser Gln Phe Val Val Ala Leu Lys
        195                 200                 205

Val Leu Phe Lys Arg Gln Ile Gly Glu Ser Asn Val Glu His Gln Val
    210                 215                 220

Arg Arg Glu Ile Glu Ile Gln Ser His Leu Arg His Pro His Ile Leu
225                 230                 235                 240

Arg Leu Tyr Ala Tyr Phe His Asp Asp Val Arg Ile Tyr Leu Ile Leu
                245                 250                 255

Glu Tyr Ala Pro Gln Gly Thr Leu Phe Asn Ala Leu Gln Ala Gln Pro
            260                 265                 270

Met Lys Arg Phe Asp Glu Arg Gln Ser Ala Thr Tyr Ile Gln Ala Leu
        275                 280                 285

Cys Ser Ala Leu Leu Tyr Leu His Glu Arg Asp Ile Ile His Arg Asp
    290                 295                 300

Ile Lys Pro Glu Asn Leu Leu Leu Gly His Lys Gly Val Leu Lys Ile
305                 310                 315                 320

```
Ala Asp Phe Gly Trp Ser Val His Glu Pro Asn Ser Met Arg Met Thr
                325                 330                 335

Leu Cys Gly Thr Val Asp Tyr Leu Pro Pro Glu Met Val Gln Gly Lys
                340                 345                 350

Pro His Thr Lys Asn Val Asp Leu Trp Ser Leu Gly Val Leu Cys Phe
                355                 360                 365

Glu Leu Leu Val Gly His Ala Pro Phe Tyr Ser Lys Asn Tyr Asp Glu
        370                 375                 380

Thr Tyr Lys Lys Ile Leu Lys Val Asp Tyr Lys Leu Pro Glu His Ile
385                 390                 395                 400

Ser Lys Ala Ala Ser His Leu Ile Ser Lys Leu Leu Val Leu Asn Pro
                405                 410                 415

Gln His Arg Leu Pro Leu Asp Gln Val Met Val His Pro Trp Ile Leu
                420                 425                 430

Ala His Thr Gln
        435

<210> SEQ ID NO 19
<211> LENGTH: 412
<212> TYPE: PRT
<213> ORGANISM: Saccharomyces sp.

<400> SEQUENCE: 19

Met Gln Arg Asn Ser Leu Val Asn Ile Lys Leu Asn Ala Asn Ser Pro
  1               5                  10                  15

Ser Lys Lys Thr Thr Thr Arg Pro Asn Thr Ser Arg Ile Asn Lys Pro
                 20                  25                  30

Trp Arg Ile Ser His Ser Pro Gln Gln Arg Asn Pro Asn Ser Gln Arg
             35                  40                  45

Asn Ser Leu Val Asn Ile Lys Leu Asn Ala Asn Ser Pro Ser Lys Lys
 50                  55                  60

Thr Thr Thr Arg Pro Asn Thr Ser Arg Ile Asn Lys Pro Trp Arg Ile
 65                  70                  75                  80

Ser His Ser Pro Gln Gln Arg Asn Pro Asn Ser Lys Ile Pro Ser Pro
                 85                  90                  95

Val Arg Glu Lys Leu Asn Arg Leu Pro Val Asn Asn Lys Lys Phe Leu
                100                 105                 110

Asp Met Glu Ser Ser Lys Ile Pro Ser Pro Ile Arg Lys Ala Thr Ser
            115                 120                 125

Ser Lys Met Ile His Glu Asn Lys Lys Leu Pro Lys Phe Lys Ser Leu
        130                 135                 140

Ser Leu Asp Asp Phe Glu Leu Gly Lys Lys Leu Gly Lys Gly Lys Phe
145                 150                 155                 160

Gly Lys Val Tyr Cys Val Arg His Arg Ser Thr Gly Tyr Ile Cys Ala
                165                 170                 175

Leu Lys Val Met Glu Lys Glu Ile Ile Lys Tyr Asn Leu Gln Lys
                180                 185                 190

Gln Phe Arg Arg Glu Val Glu Ile Gln Thr Ser Leu Asn His Pro Asn
            195                 200                 205

Leu Thr Lys Ser Tyr Gly Tyr Phe His Asp Glu Lys Arg Val Tyr Leu
        210                 215                 220

Leu Met Glu Tyr Leu Val Asn Gly Glu Met Tyr Lys Leu Leu Arg Leu
225                 230                 235                 240

His Gly Pro Phe Asn Asp Ile Leu Ala Ser Asp Tyr Ile Tyr Gln Ile
                245                 250                 255
```

```
Ala Asn Ala Leu Asp Tyr Met His Lys Lys Asn Ile Ile His Arg Asp
            260                 265                 270
Ile Lys Pro Glu Asn Ile Leu Ile Gly Phe Asn Asn Val Ile Lys Leu
            275                 280                 285
Thr Asp Phe Gly Trp Ser Ile Ile Asn Pro Pro Glu Asn Arg Arg Lys
            290                 295                 300
Thr Val Cys Gly Thr Ile Asp Tyr Leu Ser Pro Glu Met Val Glu Ser
305                 310                 315                 320
Arg Glu Tyr Asp His Thr Ile Asp Ala Trp Ala Leu Gly Val Leu Ala
                    325                 330                 335
Phe Glu Leu Leu Thr Gly Ala Pro Pro Phe Glu Glu Glu Met Lys Asp
                340                 345                 350
Thr Thr Tyr Lys Arg Ile Ala Ala Leu Asp Ile Lys Met Pro Ser Asn
            355                 360                 365
Ile Ser Gln Asp Ala Gln Asp Leu Ile Leu Lys Leu Leu Lys Tyr Asp
            370                 375                 380
Pro Lys Asp Arg Met Arg Leu Gly Asp Val Lys Met His Pro Trp Ile
385                 390                 395                 400
Leu Arg Asn Lys Pro Phe Trp Glu Asn Lys Arg Leu
                405                 410
```

CELL CYCLE-REGULATING PROTEINS

FIELD OF THE INVENTION

The present invention relates to a gene encoding a novel cell cycle control protein AIM-1 (aurora and IPL-1 like midbody-associated protein kinase), recombinant vectors containing said gene, cells transformed with said vectors, processes for producing AIM-1 using said gene and recombinant AIM-1 proteins obtained by said processes. The present invention also relates to oligonucleotide or peptide nucleic acids capable of specifically hybridizing to a nucleotide sequence encoding AIM-1 protein, antibodies recognizing AIM-1, therapeutic agents for diseases associated with abnormal cell growth comprising an inhibitor against AIM-1 protein, and screening methods for materials having serine-threonine inhibitory activity using AIM-1 gene or AIM-1 protein.

PRIOR ART

Mitosis is a fundamental mode of nuclear division of eukaryotic cells and a highly coordinated process by which eukaryotic cells assure the fidelity of chromosome segregation. The number of chromosomes is often a multiple of the basic number unique to the species, but errors during mitosis result in an individual having one to several chromosomes added to or deleted from the multiple (aneuploid), which may cause cell death or oncogenesis.

Aurora (Glover et al., Cell 81:95–105, 1995) in Drosophia (Drosophia melanogaster) and its most closely related IPL-1 (Francisco et al., Mol. Cell. Biol. 14:4731–40, 1994) in budding yeast (Saccharomyces cerevisiae) are molecules participating in M phase of mitosis and are thought to be required for high-fidelity chromosome segregation.

However, no molecules corresponding to aurora or IPL-1 have been so far reported in mammals. If a gene encoding a molecule controlling the cell cycle in mammals were available and its functions explained, it would be very interesting for pharmaceutical applications such as anticancer agents.

An object of the present invention is to search for a molecule controlling the cell cycle in mammals to determine the nucleotide sequence of a gene encoding the same, produce such a molecule by gene recombinant techniques using a recombinant vector containing said sequence, and show a potential for development of novel medicaments by constructing a screening system or the like using the same.

SUMMARY OF THE INVENTION

The inventors succeeded in isolating a gene encoding a novel cell cycle control protein kinase AIM-1 (aurora and IPL-1 like midbody-associated protein kinase) by screening a cDNA library of rats using a conserved sequence in serine-threonine kinase domain (FEBS LETT. 320:246–250, 1993) as a probe, and in explaining its functions.

Accordingly, the present invention provides a DNA containing a nucleotide sequence encoding the amino acid sequence shown as SEQ ID NO: 2 in Sequence Listing, or a nucleotide sequence encoding a protein having the amino acid sequence shown as SEQ ID NO: 2 in Sequence Listing with partial substitution, deletion or addition and having cell cycle control activity, or a nucleotide sequence hybridizing to them.

The present invention also provides a recombinant vector containing a gene encoding AIM-1 protein.

The present invention also provides a prokaryotic or eukaryotic host cell transformed with a recombinant vector containing a gene encoding AIM-1 protein.

The present invention also provides a process for producing AIM-1 protein, comprising culturing a cell transformed with a recombinant vector containing a gene encoding AIM-1 protein, and isolating and purifying the target protein produced.

The present invention also provides a recombinant AIM-1 protein produced by said process.

The present invention also provides an oligonucleotide or peptide nucleic acid capable of specifically hybridizing to a gene encoding AIM-1 protein.

The present invention also provides an antibody recognizing a peptide having at least five continuous amino acids in the amino acid sequence shown as SEQ ID NO: 2 in Sequence Listing.

The present invention also provides a therapeutic agent for diseases associated with abnormal cell growth comprising an inhibitor against AIM-1 protein.

The present invention also provides a screening method for materials having serine-threonine inhibitory activity using AIM-1 gene or AIM-1 protein.

We also tested how AIM-1 is expressed during each stage of cell division and examined the role of AIM-1 in the cell cycle.

BRIEF DESCRIPTION OF THE DRAWINGS

FIG. 1. Comparison of the amino acid sequence of AIM-1 (SEQ ID NO: 4) with the amino acid sequences of aurora gene derived from Dorosophia and IPL-1 gene derived from yeast.

FIG. 3. Staining of NRK-49F cells with anti-AIM-1 polyclonal antibody prepared in Example 5 (left column), anti-α-tubulin monoclonal antibody (middle column), or a dye Hoechst 33258 for DNA staining (right column) (photographs showing organic morphology). (a) Interphase. (b) Prophase. (c) Metaphse. (d) Late anaphase. (e) Telophase. (f) Cytokinesis. (g) Mink lung epithelial (MvlLu) cells carrying pUHD10-3/FLAG-AIM-1 (WT) prepared in Example 7 were grown in a doxycycline-free medium for 24 hours and then similarly stained with anti-FLAG monoclonal antibody M2 (KODAK) (left column), anti-α-tubulin monoclonal antibody (middle column), or Hoechst 33258 (right column).

DETAILED DESCRIPTION OF THE INVENTION

Figure 2A:
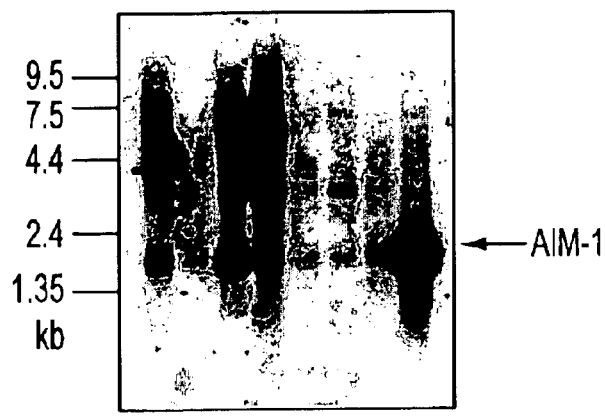
FIG. 2. a) Northern blot analysis (electrophoretogram) obtained by hybridizing poly (A) $^+$RNA isolated from various rat tissues to a $^{32}$P-labeled AIM-1 cDNA fragment. b) Relationship between the expression pattern of AIM-1 mRNA and the cell cycle (electrophoretogram). c) Analysis of change of AIM-1 protein level in NRK-49F cells at various instants of the cell cycle using an antibody against a peptide consisting of C-terminal 13 amino acids of AIM-1 sequence (electrophoretogram).

In the present invention, a cDNA encoding AIM-1 was obtained as follows.

A rat cDNA library was used as a template for PCR with oligonucleotide primer 1 sense to the conserved sequence MHRDVKP (SEQ ID NO: 3) in serine-threonine kinase domain and oligonucleotide primer 2 antisense to DFGVSGQ (SEQ ID NO: 4) as primers. A cDNA fragment was obtained by separation of the PCR products by agarose gel electrophoresis and identified.

A rat NRK-49F fibroblast cDNA library was screened by polymerase chain reaction (PCR) to isolate VI-VII subdomain of serin-threonine type protein kinase. Three full-length clones were identified by screening $1 \times 10^6$ clones of the same library with said CDNA fragment (SEQ ID NO: 1) as a probe. The sequence of the cDNA of AIM-1 is shown as SEQ ID NO: 2 together with a putative amino acid sequence thereof.

Figure 1:
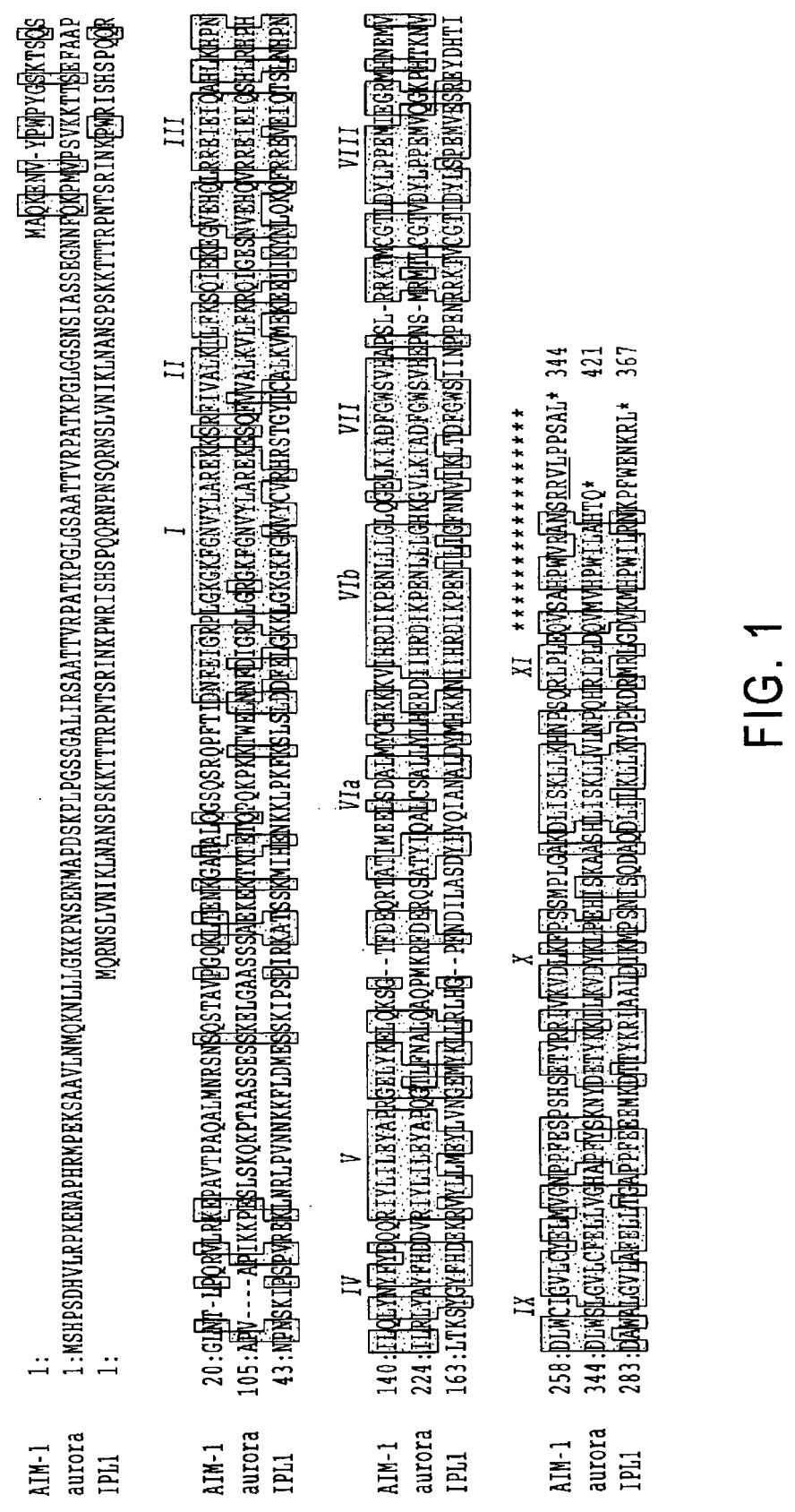

The amino acid sequence of AIM-1 consists of 344 amino acids and has a molecular weight of 39.2 kD. Its N-terminal 80 amino acid residues form a protein kinase catalytic domain of the serine-threonine type with homology to aurora of Drosophia and IPL-1 of yeast (Hanks et al., Science 241:42–52, 1988). FIG. 1 shows a comparison of the catalytic domain of AIM-1 gene with those of aurora and IPL-1 genes. The catalytic domain of AIM-1 shows identity at 60% and 46% with aurora and IPL-1, respectively, but their N-terminal amino acid sequences are not similar.

Human AIM-1 cDNA can be obtained by screening a cDNA library prepared from human tissues thought to be rich in AIM-1 (for example, highly proliferative tissues such as testis, lung and spleen) using the rat AIM-1 cDNA fragment of the present invention as a probe. In the present invention, a human cDNA was isolated by screening human intestine- and heart-derived CDNA libraries by this procedure. Human AIM-1 protein encoded by the human cDNA had identity of 81% of amino acids with rat AIM-1. Moreover, human AIM-I protein showed cell cycle control activity similar to that of rat AIM-1 as described in Example 10, suggesting that it might be a homologue of rat AIM-1.

A gene encoding AIM-1 protein of the present invention thus obtained can be used to produce large amounts of AIM-1 protein by gene recombinant techniques for pharmaceutical applications.

Namely, prokaryotic or eukaryotic host cells can be transformed by integrating a gene encoding AIM-lprotein of the present invention into appropriate vectors.

Moreover, the gene can be expressed in various host cells by introducing an appropriate promoter or a sequence participating in gene expression into these vectors. Furthermore, a target protein can be excised by expressing a fusion protein of a gene of interest coupled to a gene encoding another polypeptide for easy purification or increased expression or applying an appropriate treatment during a purification step.

As known in human interferon genes, eukaryotic genes are generally thought to show polymorphism, whereby one or more amino acids may be changed or the nucleotide sequence may be changed with no change in amino acids.

Even a polypeptide having the amino acid sequence shown as SEQ ID NO: 2 in Sequence Listing with one or more amino acids deleted or added or substituted may have cell cycle control activity. For example, it has been already known that a polypeptide obtained by changing the nucleotide sequence corresponding to cystein of human interleukin 2 (IL-2) gene into a nucleotide sequence corresponding to serine retains IL-2 activity (Wang et al., Science 224:1431, 1984). Techniques for generating these variants of the gene encoding AIM-1 protein are known to those skilled in the art.

Sugar chains often added by expression in eukaryotic cells can be controlled by changing one or more amino acids. This may also have cell cycle control activity. Therefore, any gene encoding a polypeptide obtained by using an artificial variant of the gene encoding AIM-1 protein of the present invention is included in the present invention, so far as it has cell cycle control activity.

Genes hybridizing to the gene shown as SEQ ID NO: 2 are also included in the present invention so far as the resulting polypeptides have cell cycle control activity. Hybridization conditions may be conventional probe hybridization conditions (for example, Molecular Cloning: A Laboratory Manual, Sambrook et al., Cold Spring Harbor Laboratory Press, 1989). A standard method involves, for example, hybridization in 6×SCC, 0.05×BLOTTO (Bovine Lacto Transfer Technique Optimizer) solution at 68°, preferably in Express Hyb™ Hybridization Solution (Clontech) solution at 60–68° for 18 hours, or in Rapid-hyb Buffer (Amersham) solution at 60–88° C. for 18 hours, as described in literature (Molecular Cloning: A Laboratory Manual, Sambrook et al., Cold Spring Harbor Laboratory Press, 1989). Genes recognized by a probe complementary to DNA of claim 1 and encoding a protein having biological functions of AIM-1 protein are also included in the present invention. Many techniques for isolating a cDNA clone having homology to the nucleotide sequence shown as SEQ ID NO: 2 using said probe with modifications of the salt concentration and/or hybridization temperature, for example, have already been established. Genes isolated by these techniques and encoding a protein having biological functions of AIM-1 protein are also included in the present invention (Molecular Cloning: A Laboratory Manual, Sambrook et al., Cold Spring Harbor Laboratory Press, 1989).

Expression vectors may include an origin of replication, a selectable marker, a promoter, an RNA splicing site, a polyadenylation signal, etc.

Among hosts used as expression systems, prokaryotic host cells include, for example, E. coli, B. subtilis, etc. Among eukaryotic host cells, eukaryotic microorganisms include, for example, yeast and Myxomycota. Insect cells such as Sf9 may also suitable as host cells. Animal cell-derived host cells include, for example, COS cells and CHO cells.

A protein produced by culturing a cell transformed with a gene encoding AIM-1 protein as described above can be intercellularly or extracellularly isolated and purified. The present invention includes not only proteins obtained from a gene containing a nucleotide sequence encoding the amino acid sequence shown as SEQ ID NO: 2 in Sequence Listing, but also proteins obtained from a gene containing a nucleotide sequence encoding the amino acid sequence of SEQ ID NO: 2 with partial substitution, deletion or addition, or a nucleotide sequence hybridizing to them, so far as they retain biological functions of AIM-1 protein, i.e. cell cycle control activity.

AIM-1 proteins can be isolated and purified by isolation and purification techniques used for common proteins. For example, various chromatography techniques, ultrafiltration, salting out, dialysis or the like can be appropriately selected and used in combination.

According to the present invention, antisense DNA can be prepared on the basis of the nucleotide sequence of a gene encoding AIM-1 protein. Antisense DNA has a complementary nucleotide sequence to mRNA and forms a base pair with mRNA to block the current of genetic information and to inhibit synthesis of the end product AIM-1 protein. Antisense DNA which can be used in the present invention is an oligonucleotide capable of specifically hybridizing to a nucleotide sequence encoding the amino acid sequence shown as SEQ ID NO: 2 in Sequence Listing.

The term "oligonucleotide" here means an oligonucleotide produced from a naturally occurring base or sugar moieties linked by inherent phosphodiester bond or an analog thereof. Thus, the first group included in this term consists of naturally occurring species or synthetic species produced from naturally occurring subunits or homologues thereof. The subunit means a combination of base-sugar linked to an adjacent subunit via phosphodiester bond or other bonds. The second group of oligonucleotides consists of analogs thereof, which mean residues having similar functions to oligonucleotides but having non-naturally occurring moieties. These include oligonucleotides chemically modified at their phosphate group, sugar moiety or 3', 5' ends to increase stability. Examples are oligophosphorothioates and oligomethylphosphonates in which one of oxygen atoms of the phosphodiester group between nucleotides is replaced by a sulfur or —$CH_3$, respectively. Phosphodiester bond may be replaced by other non-ionic and non-chiral structures. Oligonucleotide analogs may also include species containing a modified base form, i.e. purine and pyrimidine other than normally found in nature.

Oligonucleotides according to the present invention have preferably 5 to 40, more preferably 8 to 30, even more preferably 12 to 30 subunits.

In the present invention, the target site of mRNA to which an oligonucleotide hybridize is preferably a transcription initiation site, translation initiation site, intron/exon junction site or 5' capping site and should be selected to avoid steric hindrance in view of the secondary structure of mRNA.

In the present invention, peptide nucleic acids (for example, see Bioconjugate Chem. Vol. 5, No. 1, 1994) may also be used instead of oligonucleotides.

An especially preferred embodiment of the present invention is an oligonucleotide or peptide nucleic acid capable of hybridizing to a nucleotide sequence encoding the amino acid sequence shown as SEQ ID NO: 2 in Sequence Listing and inhibiting the expression of AIM-1 protein.

Oligonucleotides according to the present invention can be prepared by synthesis processes known in the art, such as a solid phase synthesis process using a synthesizer available from, for example, Applied Biosystems. Other oligonucleotide analogs such as phosphorothioates or alkylated derivatives can be prepared by similar processes (Akira Murakami et al., "Chemical Synthesis of Functional Antisense DNA", in Organic Synthetic Chemistry, 48 (3): 180–193, 1990).

Production of AIM-1 protein in animals can be inhibited by administering an oligonucleotide or peptide nucleic acid capable of specifically hybridizing to a gene encoding AIM-1 of the present invention to the animals. Growth of cancer cells can be inhibited or stopped by administering an oligonucleotide or peptide nucleic acid of the present invention to the cancer cells, because AIM-1 has necessary functions for progress of M phase of cell division as described in detail below. Oligonucleotides of the present invention can be expected to provide a therapy effective not only for cancer but other proliferative diseases also.

An antibody recognizing a peptide having at least five continuous amino acids in the amino acid sequence shown as SEQ ID NO: 2 in Sequence Listing of the present invention can be prepared by immunizing an animal with the peptide having at least five continuous amino acids in the amino acid sequence shown as SEQ ID NO: 2 in Sequence Listing as an antigen and collecting and purifying an antibody produced in vivo, according to a conventional procedure (for example, see New Biochemical Experiment Textbook, Vol. 1, Proteins I, pp. 389–397, 1992). Antibodies include polyclonal and monoclonal antibodies, and techniques for preparing them are also known to those skilled in the art. Thus obtained anti-AIM-I antibodies can be used in various immunological assays such as enzyme immunoassay such as ELISA, radioimmunoassay, immunofluorescence assay, or purification via a column of AIM-1 protein.

According to the present invention, growth of cancer cells or diseases associated with abnormal cell growth such as psoriasis can be inhibited or stopped by administering an inhibitor against AIM-1 (for example, an antagonist or antibody such as AIM-1 (K-R) or protein kinase activity inhibitor, or an antisense strand) to the cancer cells.

Moreover, gene therapy for inhibiting or stopping growth of cancer cells can be expected by site-specifically administering a gene encoding AIM-1(K-R) protein produced by the present invention to the cancer cells to express it at the site of the cancer cells.

According to the present invention, a screening method for materials having serine-threonine kinase inhibitory activity can be performed using AIM-1 gene or AIM-1 protein. For example, a substrate (for example, myosin light chain, histone protein, synthetic substrate), AIM-1 protein and an inhibitor candidate or a solvent are incubated in a reaction solution containing [$\gamma$-$^{32}$P]ATP at 30° C. for several minutes, for example, then the reaction is quenched by immersing Wattmann 3MM filter paper impregnated with a part of the reaction solution in ice-cooled 10% TCA- 1% sodium pyrophosphate. The filter paper is washed and dried, and then placed in a toluene scintillator to measure $^{32}$P taken up into the protein by a liquid scintillation counter and evaluate inhibitory activity from loss of the measured $^{32}$P value relative to the solvent control group.

Functions of AIM-1 Protein

AIM-1 gene expression was tested by northern blot analysis (FIG. 2a). Poly(A) $^+$RNA isolated from various rat tissues were hybridized with a $^{32}$P-labeled AIM-1 cDNA fragment. A band of AIM-1 of about 2.0 kb was detected in all the tissues tested, particularly abundantly in testis, spleen and lung.

Figure 2B:
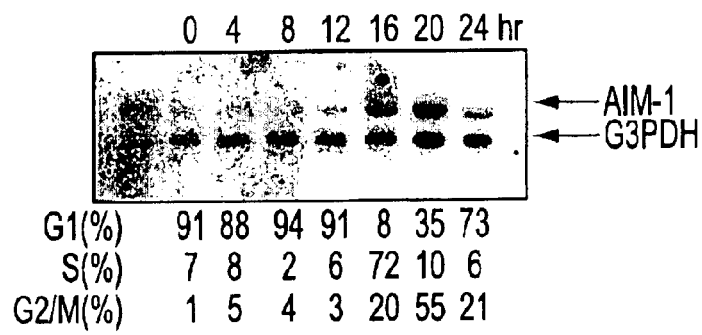

Since aurora and IPL-1 are known to participate in the progress of M phase of mitosis (chromosome segregation), we investigated whether AIM-1 expression pattern shows cell cycle-dependent oscillation. As a result, mRNA of AIM-1 was induced at late-S and peaked at G2-M transition (FIG. 2b). When M phase was arrested by colcemid treatment, a marked accumulation of AIM-1 mRNA was induced (data not shown). These results suggest that AIM-1 functions during M phase.

Figure 2C:
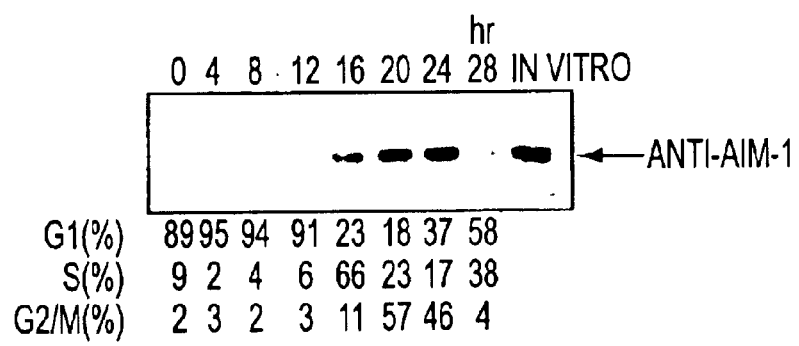

To study functions of AIM-1 protein, an antibody against a synthetic peptide of C-terminal 13 amino acids of AIM 1 sequence was prepared. Using this antibody, change of AIM-1 protein level in NRK-49F cells at various instants of the cell cycle was analyzed (FIG. 2c). The results showed that AIM-1 protein detected as a band of about 40 Kd began to accumulate at S/G2 boundary, reached the maximum level at M phase and dramatically decreased at the next G1 phase. Similar results were obtained in cells synchronized by double thymidine block and release. These data are consistent with the northern blot data. Namely, these data show that AIM-1 protein is most prominently expressed in M phase of cell division. Since the C-terminus of AIM-1 contains a consensus sequence for putative destruction box recognized by proteasome (FIG. 1), AIM-1 might undergo ubiquitin proteasome-dependent proteolysis like other G2-M phase-regulating proteins such as cyclin B (Glotzer et al., Nature 349:132–138, 1991) and cut 2 (Funabiki et al., Nature 381:438–441, 1996).

To examine how AIM-1 protein participates in the mitotic machinery during the cell cycle, asynchronously growing NRK-49F cells were immunocytochemically studied with an antibody against AIM-1. In metaphase, no signals of AIM-1 protein were detected (FIGS. 3a–c). In late anaphase, however, AIM-1 began to be detectable as a distinct band extending across the midzone of central spindle (FIG. 3d). In telophase and as cytokinesis progresses, AIM-1 protein increasingly concentrates at the midbody (FIGS. 3e, f).

Similar results were observed when FLAG-AIM-1 fusion protein fused to FLAG peptide was induced under the control of a tetracycline inducible system (Gossen and Bujard, Proc. Natl. Acad. Sci. USA 89:5547–51, 1992) in mink lung epithelial (MvlLu) cells (FIG. 3g). Immunodetection of the induced FLAG-AIM-1 with anti-FLAG antibody also demonstrated FLAG-AIM-1 localized at the midbody. This indicates that this anti-AIM-1 antibody specifically recognizes AIM-1 protein and that AIM-1 localizes at the midbody.

Since γ-tubulin has been so far identified in the midbody microtuble organizing centers (Shu et al., J.C.S. 108:2955–62, 1995), we determined subcellular localization of γ-tubulin in MvlLu Cells expressing FLAG-AIM-1. As shown in FIG. 3d, FLAG-AIM-1 protein and γ-tubulin colocalized at the midbody. These data suggest that the appearance of AIM-1 protein in mitotic cells coincides with the kinetics of protein expression shown by western blot, and that AIM-1 might regulate the cytokinetic process from anaphase to telophase.

To further investigate this possibility, we prepared inactivated FLAG-AIM-1 (K-R) in which the lysine residue at the 109-position of AIM-1 was replaced by arginine by point mutagenesis to block endogenous protein kinase activity. We also used a system inducible with tetracycline in MvlLu cells.

Figure 4A:
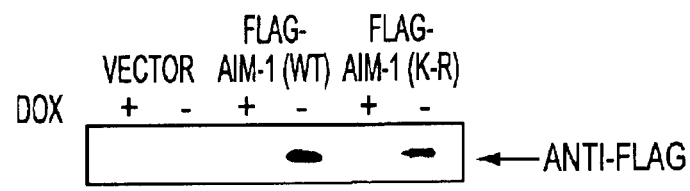
FIG. 4. A) Wild-type FLAG-AIM-1 (WT) or inactivated FLAG-AIM-1 (K-R) was induced in MvlLu cells and the cells were cultured for 18 hours after removal of doxycycline (DOX) and harvested. Cell lysates were immunoblotted with anti-FLAG monoclonal antibody (electrophoretograph). B) Asynchronous cells transfected with vector alone (a, d), FLAG-AIM-1 (WT) (b, e) or FLAG-AIM-1 (K-R) (c, f) were grown with (a–c) or without (d–f) DOX for 72 hours and stained with Giemsa's solution (photograph showing organic morphology).
In FIG. 4B, upper panels are denoted as a, b and c from left to right, and lower panels are called as d, e and f from left to right. C) Cell samples were harvested and fixed with ethanol, stained with propidium iodide for FACS analysis.
Figure 4B:
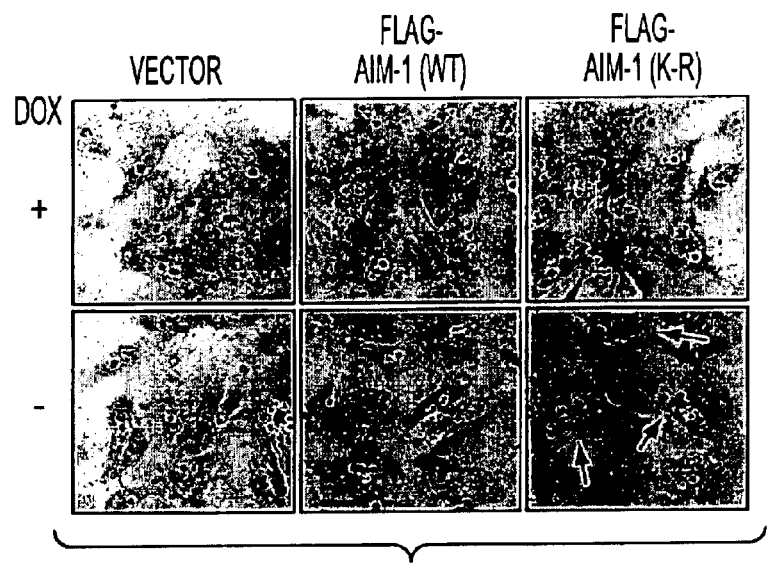
Figure 4C:
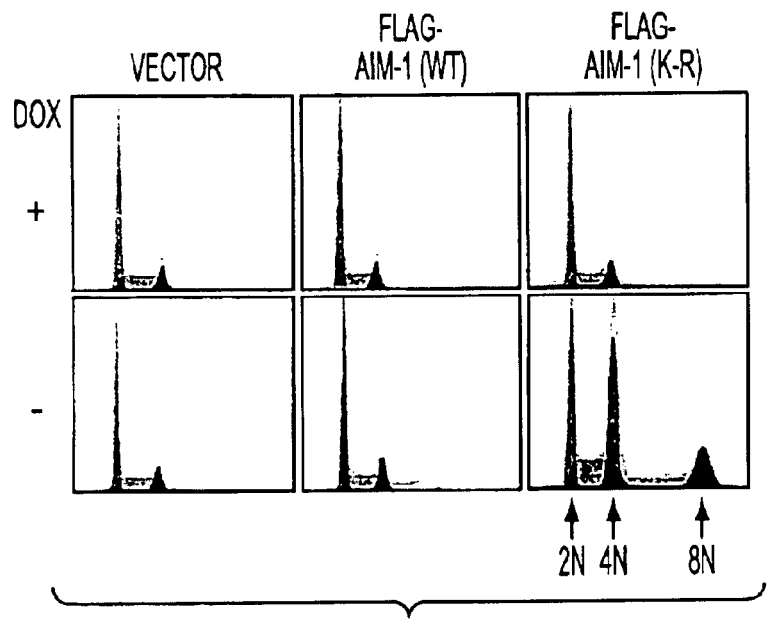

MvlLu cells carrying vector alone, wild-type FLAG-AIM-1 (WT) or FLAG-AIM-1 (K-R) were grown in the presence or absence of doxycycline (tetracycline analog) for 24 hours and then subjected to western blot with anti-FLAG antibody (FIG. 4A). When FLAG-AIM-1 (K-R) was induced for 72 hours, about 68% of cells failed to complete normal cytokinesis and had two or more nuclei (FIG. 4Bf, Table 1). In addition, the size of these cells was much larger than normal cells (FIGS. 4Bf and 5D). In these abnormal cells, however, spindle. functions including chromosome disjunction and late anaphase spindle elongation as well as nuclear division appeared unaffected (data not shown). This was further confirmed by flow cytometry (FACS) (FIG. 4C). Cell population with 4N or 8N DNA dramatically increased after 72 hour-induction of AIM-1 (K-R), suggesting the appearance of bi-nucleated or tetra-nucleated cells. Namely, apocytes appeared because karyokinesis advances but cytokinesis is inhibited.

In contrast, cells expressing wile-type FLAG-AIM-1 (WT) or cells transfected with vector alone showed a normal cell cycle pattern (FIG. 4C).

To confirm the generality of this observation, AIM-1 (WT) and AIM-1 (K-R) plasmids were transiently expressed in NRK-49F cells and human diploid fibroblast KD cells and the results were compared with those obtained in a control transfected with vector alone. These constructs were transfected into cell-s with a reporter construct RSV-⊖-galactosidase to prepare β-galactosidase-expressing plasmids for use as a positive internal control for transfection (Table 1). Transfection of vector alone did not affect normal progress of the cell cycle, but transfection of the AIM-1 (K-R) construct increased cells having two or more nuclei (NRK-49F cells: 62%; KD cells: 38%).

Figure 5D:
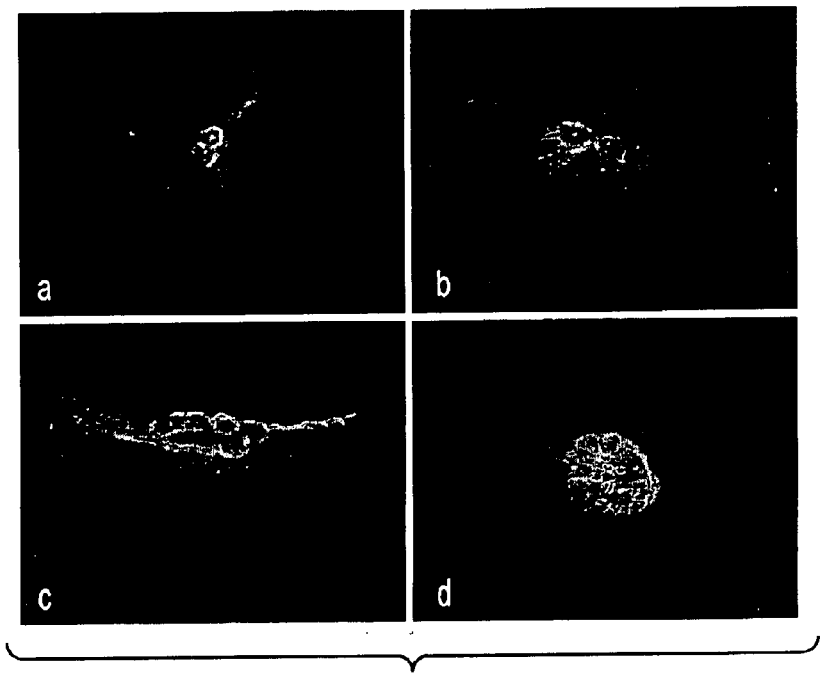
FIG. 5. D) Double staining with α-tubulin (green) and DNA (red) (propidium iodide) obtained by superimposing the images of MvlLu cells expressing FLAG-AIM-1 (K-R) shown in FIG. 4B (photographs showing organic morphology). After removal of doxycycline, abnormal cells having two (a), four (b), eight (c) or ten or more nuclei appeared. E) MvlLu cells transfected with FLAG-AIM-1 (WT) or FLAG-AIM-1 (K-R) were grown with or without DOX for 2 weeks and stained with Giemsa's solution (photographs showing organic morphology).
Figure 5E:
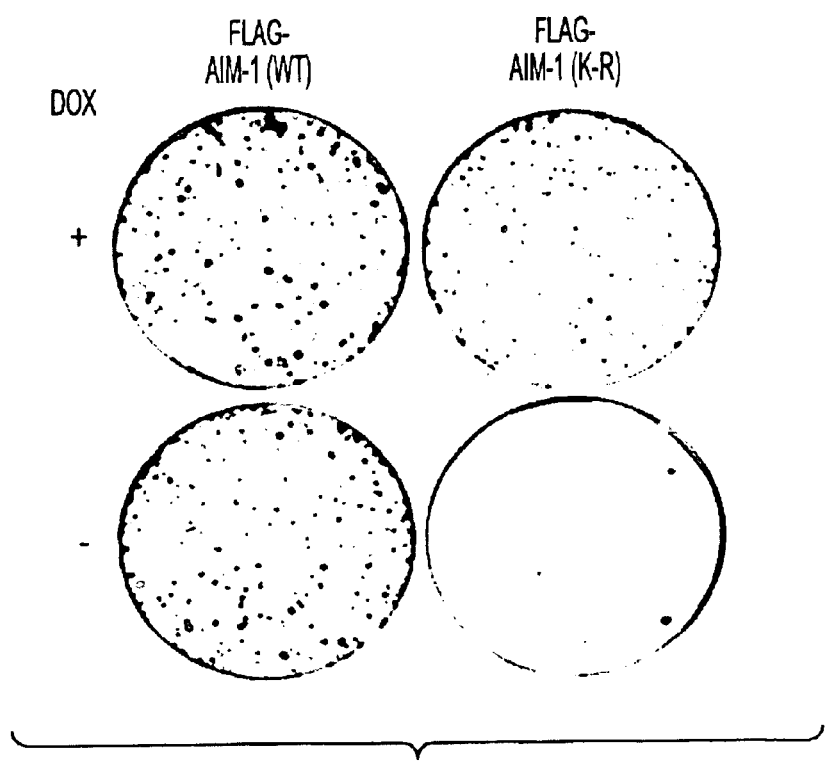

The nuclei of these AIM-1 (K-R)-expressing cells divided 3 to 4 times during 4 to 5 days, resulting in more than 10 nuclei per cell (FIG. 5D). However, these multinucleated cells did not divide further and failed to adhere to the plate. When cells were grown for 2 weeks in the presence or absence of doxycycline to determine the effects of AIM-1 (K-R) on growth potency, miotic inhibition was observed in MvlLu cells expressing AIM-1 (K-R) but not in cells expressing AIM-1 (WT) (FIG. 5E).

These data strongly suggested that overexpression of function-deficient AIM-1 inhibited cytokinesis during mitotic division to result in the appearance of apocytes, i.e. AIM-1 is required for cytokinesis.

However, these data concerning AIM-1 are in contrast to the aurora gene mutations, which show abnormal mitotic spindles due to the failure of centrosomes to separate and form bipolar spindles. This suggests that AIM-1 gene is rather a functionally related molecule than a complete functional homologue of aurora gene. Spindle functions such as centrosome separation and cytokinesis are reported to be regulated by kinesin-like proteins (KLP) (Goldstein, Trends Cell Biol. 1:93–98, 1991; Moore & Endow, BioEssays 18:207–219, 1996). A report shows that, in Drosophia, KLP-61F is required for centrosomal duplication whereas KLP-3A is a component of the midbody and required for central spindle structure and cytokinesis (Williams et al., J. Cell Biol. 129:709–723, 1995). The phenotypes in both KLP-61F and aurora mutants show strikingly similar abnormalities of the centrosomes (Heck et al., J. Cell Biol. 123:665–679, 1993), thus suggesting that they participate in a common process. Aurora kinase seems to participate in the function of KLP-61F to regulate the kinesin motor activity. In contrast, the phenotype of KLP3A mutations resembles that of AIM-1 loss-of function mutants. Therefore, AIM-1 might be implicated in the regulation of KLP-3A in cytokinesis.

Mutations in Drosophia melanogaster polo cause abnormal mitotic and meiotic divisions due to abnormal spindle formation (Fenton et al., Nature 363:637–640, 1993). This seems to lead to polipoidy. Polo-related mammalian M phase-specific protein Plk localizes at the midbody during telophase and cytokinesis (Clay et al., Proc. Natl. Acad. Sci. USA 90:4882–4886, 1993; Lee et al., Mol. Cell. Biol. 15:7143–7151, 1995; Golsteyn et al., J. Cell Biol. 129:1617–1628, 1995). These features shown by polo and PLK are similar to those of AIM-1, though they are not structurally homologous to AIM-1.

AIM-1 was observed to colocalize with γ-tubulin at the midbody during telophase and cytokinesis. Recently, the depletion of γ-tubulin using antisense RNA methods has been reported to cause a failure in morphogenesis of midbody structure and abortive cytokinesis (Shu et al., J.C.S. 108:2955–62, 1995). These data provide some links between AIM-1 and γ-tubulin. Thus, γ-tubulin may be involved in biogenesis of midbody structure in completion of cytokinesis in cooperation with AIM-1.

The following examples further illustrate the present invention without, however, limiting the same thereto.

EXAMPLES

In the following examples, cell extracts were prepared as follows.

Cells were extracted with RIPA buffer (10 mM Tris-HCl (pH 7.5), 1% NP-40, 150 mM NaCl, 1 mM EDTA, 1 mM PMSF, 4 mg/ml leupeptin), followed by centrifugation at 100,000×g for 1 hour. The obtained pellets were suspended in SDS-PAGE sample buffer, boiled and then sonicated. The supernatant obtained after centrifugation at 10,000 rpm was treated with SpinBind (FMC) to remove contaminating DNA fragments.

Example 1

Identification of a cDNA Fragment Encoding a Part of AIM-1 Gene

Oligonucleotide primer 1 sense to a conserved sequence MHRDVKP (SEQ ID NO: 5) in serine-threonine kinase domain and oligonucleotide primer 2 antisense to DFGVSGQ (SEQ ID NO: 6) were prepared. The sequences of primers 1 and 2 are as follows.
Primer 1: 5'-ATGCA(T/C)(C/A)G(T/C/A/G)GA(T/C)GT(T/C/A/G)AA(A/G)CC-3'(SEQ ID NO: 7)
Primer 2: 5'-TG(T/C/A/G)CC(T/C/A/G)GA(T/C/A/G)AC(T/C/A/G)CC(A/G)AA(A/G) TC-3' (SEQ ID NO: 8).

A rat cDNA library (FEBS LETT. 320:246–250, 1993) was used as a template for amplification by 40 cycles of PCR with vent DNA polymerase using said primers 1 and 2 as primers under conditions of 94° for 1 minute, 55° C. for 1 minute and 72° C. for 2 minutes. The PCR products were separated by agarose gel electrophoresis to give a fragment.

The CDNA fragment was sequenced to give the sequence shown as SEQ ID NO: 1 (attcacagagacataaagcccgagaacctgctgttaggtctacagggagagctgaagat tgcggactttggctggtctgtgcat).

Example 2

Library Screening
(1) Preparation of a Rat NRK-49F cDNA Library
NRK-49F RNA in logarithmic growth phase was extracted by guanidine method and mRNA was purified on an oligo-dT cellulose column. Oligo-dT/Not1 was used as a primer to synthesize CDNA with a reverse transferase. After an EcoRI adapter was ligated, the cDNA was inserted into an expression vector pcTerraIII (FEBS LETT. 320:246–250, 1993).
(2) Screening
The sequence of the cDNA fragment obtained in Example 1 (SEQ ID NO: 1) was used as a probe for gene screening.

The probe was labeled with $^{32}$-p and hybridized with the NRK-49F cDNA library coupled to filters to isolate positive clones under the following conditions. Hybridization solution: 6×SSPE, 0.5% SDS, 10×Denhardt solution, 100 u/ml denatured herring sperm DNA. The filters were washed with 2×SSC, 0.1% SDS for 15 minutes and 0.2×SSC, 0.1% SDS for 15 minutes.

Thus, three full-length cDNA clones were isolated and sequenced. The cDNA sequence of AIM-1 is shown as SEQ ID NO: 2 together with a putative amino acid sequence therefrom.

FIG. 1 shows a comparison of the amino acid sequence of AIM-1 with the amino acid sequences of aurora gene derived from Drosophia and IPL-1 gene derived yeast. In the figure, amino acid numbers are shown on the left. Roman numbers above the amino acid sequences show the kinase subdomains described by Hanks et al. (Science 241:42–51, 1988). Identical amino acid residues conserved among two or more sequences are in black. The underlined amino acid sequence in AIM-1 subdomains Vib to VII shows the sequence first identified by PCR. The amino acid sequence marked with asterisks was used to prepare the antipeptide antibody N12 described in the examples below. The underlined short stretch of the C-terminal AIM-1 amino acid sequence is a putative descruction box site.

Example 3

Expression of AIM-1 Gene in Rat Tissues

Membrane filters containing mRNA (2 μg) prepared from various rat tissues were subjected to northern blot analysis with the $^{32}$P-labeled AIM-1 cDNA fragment described in Example 2 as a probe.

Results are shown in FIG. 2a. A band of AIM-1 of about 2.0 kb was detected in all the tissues tested, particularly abundantly in testis, spleen and lung.

Example 4

Relationship Between AIM-1 mRNA and the Cell Cycle

Confluent rat NRK-49F cells were placed in serum-free medium for 2 days, then inoculated into serum-containing DMEM medium at a ratio of 1:3 to synchronously progress the cell cycle. At various instants of the cell cycle (after 0, 8, 12, 16, 20 and 24 hours), 2 μg of poly(A) $^+$RNA was added. G3PDH gene probe (Nippon Gene) was used as a control. Results are shown in the upper panel in FIG. 2b.

FACS analysis with Cycle Test (Becton Dickinson) and FACScan (Becton Dickinson) were used to calculate the percentage of the number of cells at each cell cycle stage to the total number of cells, and results are shown below the panel in FIG. 2b.

As shown in the figure, AIM-1 mRNA was induced at late-S and peaked at G2-M transition.

Example 5

Preparation of an Antibody Against AIM-1

For the preparation of a polyclonal antibody against AIM-1, a peptide of the region marked with asterisks in the amino acid sequence of AIM-1 shown in FIG. 1 (V to C-terminal L) was synthesized, coupled to KLH (keyhole limpet hemocyanin) and injected into rabbits.

Serum was obtained from the rabbits and purified on peptide-immobilized FMP activated cellulose column (Seikagaku) to give a polyclonal antibody.

Example 6

Relationship Between AIM-1 Protein Expression and the Cell Cycle

In the same manner as described in Example 4 above, the cell cycle was synchronously progressed. At various instants of the cell cycle (after 0, 4, 8, 12, 16, 20 and 24 hours), insoluble protein fractions corresponding to $2 \times 10^5$ cells were removed and subjected to western blot analysis using the anti-AIM-1 antibody (N12) prepared in Example 5 as a probe. An in vitro transcription/translation product of AIM-1 (Promega) was used as a control.

Results are shown in FIG. 2c, in which AIM-1 protein detected as a band of about 40 Kd began to accumulate at S/G2 boundary, reached the maximum level at M phase and dramatically decreased at the next G1 phase.

Similar results were obtained in cellular proteins prepared by synchronizing the cell cycle by double thymidine block and release.

Example 7

Construction of Expression Plasmids (1) Preparation of FLAG-AIM-1 (WT)

The full-length coding sequence of AIM-1 cDNA obtained in Example 2 was subcloned into plasmid pUHD10-3 (obtained from Hermann Bujard, Zentrum fur Moleculare Biologie der Universitat Heidelberg, Im Neuenheimer Feld 282, W-6900, Heidelberg, Federal Republic of Germany) or pEF/hygI containing EFla promoter (Mizushima et al., Nucleic Acids Res. 18:5322, 5326, 1990) to prepare FLAG-AIM-1 (WT) labeled with FLAG protein at the N-terminus.

(2) Preparation of FLAG-AIM-1 (K-R)

FLAG-AIM-1 (K-R) was prepared by two-step PCR using the following primers.

Primer 3: 5'-AGA GAA TTC ATG GAC TAC AAG GAC GAT GAC GAC AAG ATG GCT CAG AAA GAG AAC-3' (SEQ ID NO: 9)

Primer 4: 5'-CTT GAA GAG GAT CCT TAG CGC CAC GAT-3' (SEQ ID NO: 10)

Primer 5: 5'-ATC GTG GCG CTA AGG ATC CTC TTC AAG-3' (SEQ ID NO: 11)

Primer 6: 5'-GA CTC AGA CTA AAG GGC AGA GGG AGG CAG ACG GCG GC-3' (SEQ ID NO: 12)

First PCR (A) AIM-1 gene was used as a template for amplification with a combination of primer 3 and primer 4 to give a fragment of 330 bp, which was then purified by agarose gel electrophoresis.

(B) Separately, AIM-1 gene was used as a template for amplification with a combination of primer 5 and primer 6 to give a fragment of 700 bp, which was then purified by agarose gel electrophoresis.

Second PCR

Equal amounts of the above fragments (A) and (B) were mixed and subjected to PCR with a combination of primer 3 and primer 6 to give a fragment of 1.03 kb, which was then purified, cleaved at EcoRI and XbaI sites and inserted into multicloning sites of pUHD10-3.

(3) Expression of Plasmids FLAG-AIM-1 (WT) prepared in (1) above and FLAG-AIM-1 (K-R) prepared in (2) above were expressed. Then, they were cotransfected into MvlLu cells (ATCC CRL-6584) with hygromycin-resistant plasmid pEF/hygI, using Lipofectin method according to the protocol of the provider (GIBCO, BRL). Clones were selected in 0.2 mg/ml hygromycin (Calbiochem) and doxycycline (Sigma). Clones in which FLAG-AIM-1 (WT) or (K-R) was induced after 18 hours in the absence of doxycycline were selected by western blotting using anti-FLAG antibody (M2) as a probe. A clone carrying the empty vector was used as a control.

Example 8

Involvement of AIM-I Protein in Mitosis (1) Immunocytochemical test using antibodies To examine how AIM-1 protein participates in the mitotic machinery during the cell cycle, synchronously growing NRK-49F cells were immunocytochemically studied with an antibody against AIM-1.

NRK-49F cells were stained with the anti-AIM-1 polyclonal antibody prepared in Example 5 (left column in FIG. 3), anti-α-tubulin monoclonal antibody (middle column in FIG. 3), or a dye Hoechst 33258 for DNA staining (right column in FIG. 3).

Cells grown on Labtec chamber slides (Nunc) were pretreated with a microtubule-stabilizing buffer (Boleti) (MSB: 80 mM K-PIPES (pH 6.8), 5 mM EGTA, 1 mM $MgCl_2$) containing 0.5% Triton X-100 and then fixed with methanol (for 10 minutes at −20 0). Fixed cells were washed with a solution of 0.1 M PIPES (pH 7.2), 1 mM $MgSO_4$, 1 mM EGTA, 1.83% L-lysine, 1% BSA and 0.1% sodium azide, and were subsequently incubated for 1 hour with a monoclonal mouse anti-a-tubulin antibody #7-5168 (Sigma) and affinity-purified rabbit AIM-1 antibody N12, or mouse anti-FLAG monoclonal antibody (M2) and rabbit anti-a-tubulin antibody (Masuda). Then, they were incubated with FITC-conjugated goat anti-rabbit IgG antibody and rhodamine-conjugated goat anti-mouse IgG antibody. Signals were observed under microscope (Olympus).

According to the progress of cell division, FIG. 3 shows the following stages. (a) Interphase. (b) Prophase. (c) Metaphse. (d) Late anaphase. (e) Telophase. (f) Cytokinesis.

AIM-1 was not detected during metaphase, but in the midzone of central spindle during late anaphase. This staining was observed to increase at the midbody during telophase and as cytokinesis progresses.

(2) Test with Expression Plasmids

Mink lung epithelial (Mv1Lu) cells carrying pUHD10-3/FLAG-AIM-1 (WT) prepared in Example 7 were grown in a doxycycline-free medium for 24 hours and then similarly stained with anti-FLAG monoclonal antibody M2 (KODAK), anti-α-tubulin monoclonal antibody (Masuda et al., J. Cell Sci. 109:165–177, 1996), or Hoechst 33258.

As shown in FIG. 3g, FLAG-AIM-1 protein and γ-tubulin colocalized at the midbody during cytokinesis. This coincides with the protein expression pattern shown by western blot, suggesting that AIM-1 might participate in the regulation of the cytokinetic process from anaphase to telophase.

Example 9

AIM-I and Appearance of Apocytes (1) Expression of AIM-1 and cell abnormality Wild-type FLAG-AIM-1 (WT) or kinase-inactive FLAG-AIM-1 (K-R) (dominant negative type) prepared in Example 7 was induced in MvlLu cells. After removal of doxycycline (DOX), the cells were cultured for 18 hours. The cells were harvested and cell lysates were subjected to immunoblotted with anti-FLAG monoclonal antibody. Results are shown in FIG. 4A.

Then, asynchronous cells transfected with vector alone (a, d), FLAG-AIM-1 (WT) (b, e) or FLAG-AIM-1 (K-R) (c, f)

were grown with (a–c) or without (d–f) DOX for 72 hours and stained with Giemsa's solution. Results are shown in FIG. 4B, wherein upper panels are called as a, b and c from left to right, and lower panels are called as d, e and f from left to right. Expression of kinase-inactive FLAG-AIM-1 (K-R) led to the appearance of cells having two or more nuclei (FIG. 4f).

Cell samples were harvested and fixed with ethanol, stained with propidium iodide for FACS analysis. Results are shown in FIG. 4C. Cell population with 4N or 8N DNA dramatically increased after 72 hour-induction of AIM-1 (K-R), suggesting the appearance of bi-nucleated or tetra-nucleated cells.

FIG. 5D shows double staining with α-tubulin (green) and DNA (red) (propidium iodide) obtained by superimposing the images of MvlLu cells expressing FLAG-AIM-1 (K-R) shown in FIG. 4B, After removal of doxycycline, abnormal cells having two (a), four (b), eight (c) or ten or more nuclei appeared. α-Tubulin was detected by anti-α-tubulin antibody and FITC-conjugated goat anti-mouse IgG (Cappel), and signals were observed by confocal laser microscopy (Fluoview, Olympus).

Mv1Lu cells transfected with FLAG-AIM-1 (WT) or FLAG-AIM-1 (K-R) were grown with or without DOX for 2 weeks and stained with Giemsa's solution. Results are shown in FIG. 5E. As shown in the figure, miotic inhibition was observed in MvlLu cells expressing AIM-1 (K-R) but not in cells expressing AIM-1 (WT).

(2) Abnormal Cytokinesis in Cells Expressing AIM-1 (K-R)
Plasmid FLAG-AIM-1 (WT), FLAG-AIM-1 (K-R) or a control plasmid pEF/hygI was cotransfected with a reporter construct RSV-β-galactosidase at a ratio of 10:1 into NRK-49F cells and human diploid fibroblast KD cells (a kind gift of late Dr. Takeo Kakunaga) by Lipofectin method. After 24 hours, 1×10³ cells were seeded per 60 mm dish, and 72 hours after transfection, cells were fixed in 1.25% glutaraldehyde/PBS and stained by a method described in literature (Shu et al., J.C.S. 108:2955–62, 1995) to observe expression of β-galactosidase. MvlLu cells were also tested under the conditions described in (1) B above.

Results are shown in Table. 1. The figures in the table mean the percentage of cells having two or more nuclei to β-galactosidase positive cells for NRK-49F cells and KD cells or the percentage of cells having two or more nuclei to the total number of cells for MvlLu cells. For each cell line, 160 or more cells were tested.

TABLE 1

| Plasmid | NRK-49F | KD | Mv1Lu DOX(+) | Mv1Lu DOX(−) |
|---|---|---|---|---|
| Vector alone | 0.5 | 0.2 | 0.4 | 0.7 |
| AIM-1 (WT) | 7.8 | 4.8 | 0.9 | 2.8 |
| AIM-1 (K-R) | 62.0 | 38.4 | 7.7 | 68.4 |

Example 10

Isolation of Human CDNA. Expression of AIM-1 Protein and its Activity (1) Isolation of Human AIM-1

Oligonucleotide primer 7 sense to the conserved sequence IHRDIKP in serine-threonine kinase domain and oligonucleotide primer 8 antisense to DFGWSVH were prepared.

Primer 7: 5'-AT(A/T/C)CA(T/C)(A/C)G(A/T/C/G)GA(T/C)AT(A/T/C)AA(A/G)CC(A/T /C/G)-3' (SEQ ID NO: 13)
Primer 8: 5'-(A/G)TG(A/T/C/G)AC(A/T/C/G)GACCA(A/T/C/G)CC(A/G)AA(A/G)T-3' (SEQ ID NO: 14).

Human (intestine and heart) cell-derived cDNA libraries prepared by the "lone linker" technique (Abe, Mamm. Genome 2:252–259, 1992) were used as template for the amplification with ExTaq DNA polymerase (Takara, Tokyo) using said primers 7 and 8 as primers. The PCR products were subcloned to give about 50 fragments per library and the fragments were sequenced.

Based on sequence information of these cDNA fragments, oligonucleotide primer 9 sense to NLLLGLKGELKI (SEQ ID NO: 15) and universal adapter primer 10 to oligo (dT)-containing adapter primer for the construction of a CDNA libraries prepared by "lone linker" technique were prepared.

Primer 9: 5'-AATCTGCTCTTAGGGCTCAAGGGAGAGCTGAAGATT-3' (SEQ ID NO: 16)
Primer 10: 5'-TCCACTAATATCGGCCACGCGTCGACTAGTAC-3' (SEQ ID NO: 17).

These primers were used to amplify the 3' end of AIM-1 cDNA and the amplification product (550 bp) was sequenced. Then, a HeLa cDNA library (Otsu et al., FEBS Lett. 320:246–259, 1993) was screened with this amplification product as a probe to isolate and sequence a clone containing the full-length AIM-1 cDNA.

(2) Expression and Activity of AIM-I Protein

Northern blot analysis of blots containing polyadenylated RNA derived from various tissues with human AIM-1 cDNA as a probe showed high-level expression in thymus as well as expression in testis, placenta, lung, small intestine, large intestine and spleen.

Northern blot analysis of the expression level of human AIM-1 in several colorectal tumor cell lines showed high level in all the cell lines and appearance of apocytes and polyploids at high frequency (10–20%), suggesting that AIM-1 is related to formation of apocytes and increase of polyploids.

In order to confirm that expression of human AIM-1 is cell cycle-dependent, expression of AIM-1 was tested using cells treated with colcemid to reveal that AIM-1 accumulation peaked during G2/M phase.

What is claimed is:

1. An isolated DNA containing a nucleotide sequence encoding the amino acid sequence as shown in SEQ ID NO:4.

2. An isolated recombinant vector containing DNA of claim 1.

3. An isolated eukaryotic or procaryotic host cell transformed with the recombinant vector of claim 2.

4. A process of producing a recombinant protein comprising culturing the host cell of claim 3 and isolating and purifying the protein produced, wherein said protein is encoded by the DNA of claim 1.

5. The process of claim 4 wherein the recombinant protein has cell cycle control activity.

6. A recombinant AIM-1 protein obtained by isolating and purifying the culture supernatant obtained by culturing the host cell of claim 1, wherein said protein is encoded by the DNA of claim 1.

* * * * *